United States Patent [19]

Shuman et al.

[11] Patent Number: 5,439,888

[45] Date of Patent: Aug. 8, 1995

[54] ANTITHROMBOTIC AGENTS

[75] Inventors: Robert T. Shuman, Greenwood; Gerald F. Smith, Indianapolis, both of Ind.

[73] Assignee: Eli Lilly and Company, Indianapolis, Ind.

[21] Appl. No.: 206,578

[22] Filed: Mar. 4, 1994

[51] Int. Cl.⁶ .................. A61K 3/47; C07D 217/04
[52] U.S. Cl. ........................ 514/18; 514/19; 514/307; 514/210; 514/423; 530/331; 540/200; 546/144; 546/145; 548/566; 548/558
[58] Field of Search ............... 546/144, 145; 540/200; 514/210, 423, 307, 18.19; 530/331

[56] References Cited

U.S. PATENT DOCUMENTS

| | | | |
|---|---|---|---|
| 4,316,889 | 2/1982 | Bajusz et al. | 424/177 |
| 4,346,078 | 8/1982 | Bajusz et al. | 424/177 |
| 4,399,065 | 8/1983 | Bajusz et al. | 260/112.5 R |
| 4,478,745 | 10/1984 | Bajusz et al. | 260/112.5 R |
| 4,703,036 | 10/1987 | Bajusz et al. | 514/18 |
| 5,053,392 | 10/1991 | Klein et al. | 514/18 |
| 5,202,416 | 4/1993 | Steuber et al. | 530/322 |
| 5,204,323 | 4/1993 | Findlay et al. | 514/2 |
| 5,250,660 | 10/1993 | Shuman et al. | 530/344 |

FOREIGN PATENT DOCUMENTS

| | | | |
|---|---|---|---|
| 293881 | 12/1988 | European Pat. Off. | 514/210 |
| 410411 | 1/1991 | European Pat. Off. | 514/210 |
| 479489 | 4/1992 | European Pat. Off. | 514/210 |
| 526877 | 8/1992 | European Pat. Off. | 514/210 |
| 503203 | 9/1992 | European Pat. Off. | 514/210 |
| 529568 | 3/1993 | European Pat. Off. | 514/210 |
| 530167 | 3/1993 | European Pat. Off. | 514/210 |
| 542525 | 5/1993 | European Pat. Off. | 514/210 |
| WO93/08211 | 4/1993 | WIPO | 514/210 |

OTHER PUBLICATIONS

Bajusz, S., et al., *J. Med. Chem.*, 1990, 33, 1729–1735.
Fareed, J., et al., *Annals N.Y. Academy of Sciences*, 1981, 765–784.
Shuman, et al., Proceedings of the Twelfth American Peptide Symposium, Jun. 16–21, 1991.
Wilson, et al., American Heart Association, Nov. 11–14, 1991, Anaheim Convention Center, Anaheim, Calif.
Bajusz, et al., *Int. J. Peptide Res.*, 12, 1978, 217–221.
Gesellchen, et al., Tenth American Peptide Symposium, May 23–28, 1987, St. Louis, Mo.
Claeson, et al., Proceedings of the Twelfth American Peptide Symposium, Jun. 16–21, 1991, Cambridge, Mass., pp. 822–823 and 824–825.
Smith, G. F., Shuman, R. T. Gesellchen, P. D., Craft, T. J., Gifford, P., Kurz, K. D., Jackson, C. V., Sandusky, G. E., and P. D. Williams, A New Family of Thrombin Inhibitors with Improved Specificity and Therapeutic Index. (Submitted to the American Heart Association, Oct. 1991, Circulation Oct., 1991, vol. 84, II-579, 1991).
Jackson, V., Wilson, H., Frank, J., Crowe, V., Craft, T., and G. Smith. The Thrombin Inhibitor, Methyl-D--Phe-Pro-Arginal—An Effective Adjunct to Coronary Artery Thrombolysis in the Anesthetized Dog. FASEB J. 5(4)A 521 (1991).
Crowe, V., Frank, J., Wilson, H., Coffman, B., Smith, G., and V. Jackson. Anticoagulant and Antithrombotic Efficacy of the Novel Thrombin Inhibitor Methyl-D-Phg-Pro-Arginal in a Canine Model of Coronary Thrombosis. FASEB J. 5(4)A 521 (1991).
Wilson, H., Frank J., Crowe, V., Coffman, B., Smith, G., Shuman, R., and V. Jackson, Anticoagulant and Antithrombotic Efficacy of the Novel Thrombin Inhibitor, Methyl-D-Phg-Pro-Arginal, in a Canine Model of Coronary Thrombosis (Arteriosclerosis and Thrombosis, 11(5), Oct., 1991).

(List continued on next page.)

*Primary Examiner*—C. Warren Ivy
*Assistant Examiner*—Zinna N. Davis
*Attorney, Agent, or Firm*—Thomas E. Jackson; Robert A. Conrad; David E. Boone

[57] ABSTRACT

This invention relates to L-Arginine aldehyde derivatives, pharmaceutical formulations containing those compound and methods of their use as thrombin inhibitors.

15 Claims, No Drawings

OTHER PUBLICATIONS

Jackson, V., Wilson, H., Frank, J., Crowe, V., Coffman, B., Shuman, R., and G. Smith. The Novel Thrombin Inhibitor Methyl-D-Phg-Pro-Arginal: An Effective Conjunctive Agent to Coronary Artery Thrombolysis in the Anesthetized Dog. (Arteriosclerosis and Thrombosis, 11(5), Oct., 1991).

Shuman, R. T., Rothenberg, R. B., Campbell, C. S., Smith, G. F., Jackson, C. V., Kurz, K. D., and P. D. Gesellchen. Prevention of Reocclusion by a Thrombin Inhibitor. (American Peptide Symposium, Jun., 1991, pp. 799–800).

Shuman, R. T., Rothenberger, R. B., Campbell, C. S., Smith, G. F., Jackson, C. V. Kurz, K. D., and P. D. Gesellchen. A Series of Highly Active Serine Proteinase Inhibitors. (American Peptide Symposium, Jun. 1991, pp. 801–802).

Jackson, C. V., Frank, J. D., Crowe, V. G., Craft, T. J., and G. F. Smith. Assessment of the Anticoagulant and Antithrombotic Efficacy of the Thrombin Inhibitor, BOC-Phe-Pro-Arginal, in a Canine Model of Coronary Thrombosis. *Arteriosclerosis* 10 922A (1990).

Jackson, C. V., Frank, J. D., Crowe, V. G., Craft, T. J., and G. F. Smith. The Thrombin Inhibitor, BOC-D-Phe-Pro-Arginal. An Effective Adjunct to Coronary Artery Thrombolysis in the Anesthetized Dog. *Arteriosclerosis*, 10 923a (1990).

Shackelford, K. A., Tanzer, R. L., Shuman, R. Gesellchen, P. D., Grindey, G. B., Sundboom, J. L., Smith, G. F., and R. L. Merriman. Inhibition of Spontaneous Metastasis by Boc-D-Phe-Pro-Arginal. American Association for Cancer Research, San Francisco, 1989. *Proc. Am. Assn. Cancer Res.*, 30 86, 1989.

Neubauer, B. L., Clemens, J. A., Gesellchen, P. D., Hirsch, K. S., Hoover, D. M. Merriman, R. L., and G. F. Smith. Endocrine Characterization and Sensitivity of the PAIII Prostatic Adenocarcinoma in Male Lobund-Wistar (LW) Rats to Anti-Fibrin Agents. American Association for Cancer Research. New Orleans, May 1988, *Proc. Am. Assn. Cancer Res.*, 29 240 (1988).

Neubauer, Best, K. L., Gesellchen, P. D., Goode, R. L., Merriman, R. L., Tanzer, L. R., Shaar, C. J., Shuman, R., Sundboom, Pro-Arginal on the Metastasis of the PAIII Prostatic Adenocarcinoma in Male Lobund Wistar (LW) Rats. American Urological Association. Boston, May 1988, *J. Urol.*, 139 175A (1988).

Gesellchen, P. D. Smith, G. F., et al., Anticoagulant, Antithrombotic, and Antimetastatic Effects of a Serine Proteinase Inhibitor. 10th American Peptide Symposium, Washington University, St. Louis, Mo. (1987).

Smith, G. F., Sundboom, J. L., Best, K., Gesellchen, P. D., Merriman, R. L., Shuman, R., and Neubauer, B. L. Heparin, Boc-D-Phe-Pro-Arginal, and Warfarin (Fibrin Antagonists) Inhibit Metastasis in an In Vivo Model. American Chemical Society National Meeting. Abstract BIOL 70 Biochemistry (1987).

K. D. Kurz, T. Smith, R. A. Moore, and B. W. Main. Comparison of Thrombin Inhibitors in Rat Models of Thrombosis and Thrombolysis. FASEB Journal, vol. 5 (No. 4), 1991.

Tomori, et al., *Chromatographia*, vol. 19, 437–442 (1984).

Dayhoff, *Atlas of Protein Sequence and Structure* 5, pp. 85–89 (1972).

Shuman, et al., *J. Med. Chem.*, 36(3), 314–319 (1993).

Jackson, et al., *J. Cardiovasc. Pharmacol.*, 21(4), 587–594 (1993).

Cheng, et al., *Tetrahedron Lett.*, 32(49), 7333–7336 (1991).

Bagdy, et al., *Thrombosis and Haemostasis*, 68(2), 125–129 (1992).

*Thrombosis and Haemostasis* 65, 1289, Nos. 2150–2151 and 2152 (1991).

Bagdy, et al., *Thrombosis and Haemostasis*, 67(3), 325–330 (1992).

Bagdy, et al., *Thrombosis and Haemostasis*, 67(3), 357–365 (1992).

Balasubramanian, et al., *J. Med. Chem.*, 36, 300–303 (1993).

Shuman, et al., Oral Activity of Tripeptide Aldehyde Thrombin Inhibitors, Thirteenth American Peptide Symposium, Jun. 20–25, 1993.

Kurz, et al., Antithrombotic Efficacy in the Rat After Intravenous and Oral Administration of a Direct Inhibitor of Thrombin FASEB, Mar. 28–Apr. 1, 1993.

Iwanowicz, et al., *Bioorg. Med. Chem. Lett.*, 2(12), 1607–1612 (1992).

Barabas, et al., *Blood Coagul. Fibrin.*, 4, 243–248 (1993).

Jackson, et al., Conjunctive Therapy with the Thrombin Inhibitor, LY 2944468, and Aspirin Produced Enhanced Antireocclusive Activity When Used in a Canine Model of Streptokinase-Induced Coronary Thrombolysis, *The Pharmacologist*, 35(3), 207 (1993).

Pozsgay, et al., Study of the Specificity of Thrombin with Tripeptidyl-p-nitroanilide Substrates, *Eur. J. Biochem.*, 115, 491–495 (1981).

ANTITHROMBOTIC AGENTS

BACKGROUND OF THE INVENTION

This invention relates to thrombin inhibitors which are useful anticoagulants in mammals. In particular it relates to L-Arginine aldehyde derivatives having high antithrombotic activity, anticoagulant activity, and oral bioavailability.

The process of blood coagulation, thrombosis, is triggered by a complex proteolytic cascade leading to the formation of thrombin. Thrombin proteolytically removes activation peptides from the A$\alpha$-chains and B$\beta$-chains of fibrinogen, which is soluble in blood plasma, initiating insoluble fibrin formation.

Anticoagulation is currently achieved by the administration of heparins and coumarins.

Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because surface-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6-24 hours after administration. Further, they are not selective anticoagulants. Coumarins also require monitoring with coagulation assays (particularly the prothrombin time (PT) assay).

Recently, interest in small synthetic peptides that are recognized by proteolytic enzymes in a manner similar to that of natural substrates has grown. Tripeptide aldehydes such as D-Phe-Pro-Arg-H, Boc-D-Phe-Pro-Arg-H, and D-MePhe-Pro-Arg-H, Bajusz et al., *J. Med. Chem.*, 33, 1729-1735 (1990) demonstrate potent direct inhibition of thrombin. Many investigators have synthesized analogs in an effort to develop pharmaceutical agents, for example Shuman et al., *J. Med. Chem.*, 36, 314-319 (1993).

Although the heparins and coumarins are effective anticoagulants, and no drug has yet emerged from the known tripeptide aldehydes, and despite the continuing promise for this class of compounds, there exists a need for anticoagulants that act selectively on thrombin, and independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent thrombin inhibitors that may have high bioavailability following oral administration.

Accordingly, it is a primary object of the present invention to provide novel L-Arginine aldehyde derivatives that are potent thrombin inhibitors useful as anticoagulants.

Other objects, features, and advantages will be apparent to those skilled in the art from the following description and claims.

SUMMARY OF THE INVENTION

The present invention provides thrombin inhibiting compounds having the Formula

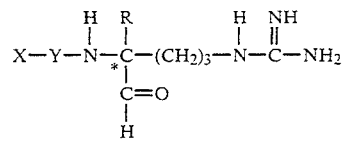

wherein
X is

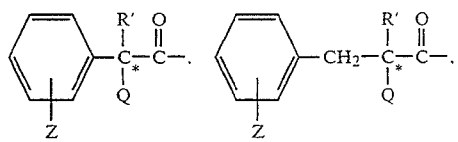

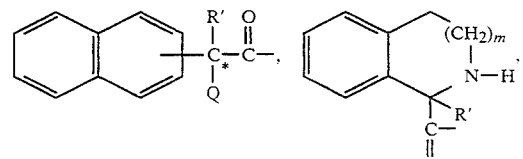

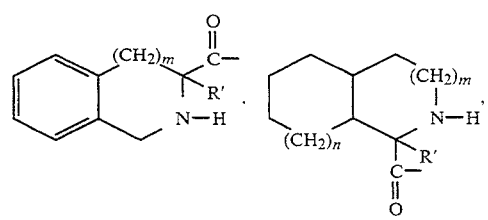

or

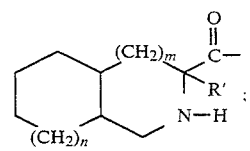

Q is —OH, $C_1$-$C_4$ alkoxy, or —NH—A;

A is hydrogen, $C_1$-$C_4$ alkyl, acetyl, $CF_3C(O)$—, $CF_3CF_2C(O)$—, R"$SO_2$—, benzyloxycarbonyl, or t-buryloxycarbonyl;

R' is hydrogen, $C_1$-$C_4$ alkyl, phenyl, or benzyl;

R" is $C_1$-$C_4$ alkyl, —$(CH_2)_d$—COOH, or unsubstituted or substituted aryl or heteroaryl (Ar), where aryl is phenyl or naphthyl, and heteroaryl is a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

d is 1, 2, or 3;
m is 0, 1, or 2;
n is 0, 1, or 2;

Y is

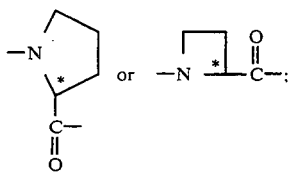

R is methyl or ethyl; and

Z is hydrogen, $C_1$–$C_4$ alkyl, $C_1$–$C_4$ alkoxy, hydroxy, halo, or $R_aSO_2NH$—, where $R_a$ is $C_1$–$C_4$ alkyl;

and pharmaceutically acceptable salts and solvates thereof.

In addition to the compounds of Formula I, the present invention provides pharmaceutical formulations comprising a compound of Formula I in association with a pharmaceutically acceptable carrier, diluent or excipient.

The present invention also provides a method of inhibiting thrombosis in mammals comprising administering to a mammal in need of treatment, an antithrombotic dose of a compound of Formula I.

The present invention further provides a method of inhibiting thrombin comprising administering to a mammal in need of treatment, a thrombin inhibiting dose of a compound of Formula I.

DETAILED DESCRIPTION OF THE INVENTION

This invention relates to new inhibitors of thrombin, pharmaceutical compositions containing the compounds as active ingredients, and the use of the compounds as anticoagulants for prophylaxis and treatment of thromboembolic diseases such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process.

The term "alkyl" by itself or as part of another substituent means a straight or branched chain alkyl radical having the stated number of carbon atoms such as methyl, ethyl, n-propyl, isopropyl, n-butyl, t-butyl, isobutyl and sec-butyl.

The term "alkoxy" means a straight or branched chain alkyl radical having the stated number of carbon atoms bonded to the parent moiety by an oxygen atom. The term "halo" means chloro, fluoro, bromo or iodo. The term "acetyl" means $CH_3$—C(O)—. The term "t-butyloxycarbonyl" means $(CH_3)_3C$—O—C(O)— and is abbreviated "Boc". The term "benzyloxycarbonyl" means $C_6H_5CH_2$—O—C(O)— and is abbreviated "Cbz".

The term "5- or 6-membered heterocyclic ring" means any 5- or 6-membered ring that will afford a stable structure containing one or two nitrogen atoms; one sulfur atom; one oxygen atom; one nitrogen and one sulfur atom; or one nitrogen and one oxygen atom. The 5-membered ring has one or two double bonds and the 6-membered ring has two or three double bonds. Such heterocyclic systems include furyl, thienyl, pyrrolyl, pyrazolyl, oxazolyl, isoxazolyl, thiazolyl, isothiazolyl, pyranyl, pyridinyl, pyrimidinyl, pyrazinyl, oxazinyl and thiazinyl.

The term "9- or 10-membered heterocyclic ring" means any bicyclic group in which any of the above 5- or 6-membered rings is fused to a benzene ring or another 6-membered heterocyclic ring as defined above that will afford a stable structure. These heterocyclic systems include indolyl, benzothienyl, benzofuryl, benzoxazolyl, benzoisoxazolyl, benzopyrazolyl, quinolinyl, isoquinolinyl, benzimidazolyl and benzothiazolyl.

It will be appreciated that many of the above heterocycles may exist in tautomeric forms. All such forms are included within the scope of this invention.

All of the aryl or heteroaryl groups listed for the definition of Ar are unsubstituted or substituted with one or two substituents that will afford a stable structure independently selected from halo, hydroxyl, $C_1$–$C_4$ alkyl, $C_1$–$C_4$ alkoxy, amino (—$NH_2$), substituted amino (—$NHR^1$), —$(CH_2)_kCOOH$, mercapto, and substituted thio (—$S(O)_hR^1$), and $R^1$ is $C_1$–$C_4$ alkyl, $C_1$–$C_4$ alkoxy, ($C_1$–$C_4$ alkyl)$S(O)_h$—, amino, $C_1$–$C_4$ alkylamino, ($C_1$–$C_4$ alkyl)—C(O)—, or ($C_1$–$C_4$ alkyl)-$SO_2NH$—, h is 0, 1 or 2, and k is 0, 1, 2, 3, or 4.

In the representation of Formula I, the carbonyl functionality of group X is attached to the amine functionality of the Y group. The carbonyl functionality of Y is then attached to the amino group drawn in Formula I.

The group

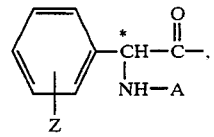

where Z and A are both hydrogen, is referred to at times herein as phenylglycyl and abbreviated Phg. Compounds wherein A is, e.g., methyl, are referred to as the N$^\alpha$ethyl-phenylglycyl group and abbreviated MePhg. Substituted compounds wherein Z is other than hydrogen are referred to by the type and position of the substituent group, e.g., 3'-chlorophenylglycyl or Phg (3-Cl).

The group

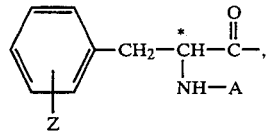

where Z and A are both hydrogen, is referred to at times herein as phenylalanyl and abbreviated Phe. Compounds wherein A is, e.g., methyl, are referred to as the N$^\alpha$methyl-phenylalanyl group and abbreviated MePhe. Substituted compounds wherein Z is other than hydrogen are referred to by the type and position of the substituent group, e.g., 3'-chlorophenylalanyl or Phe (3-Cl).

The groups

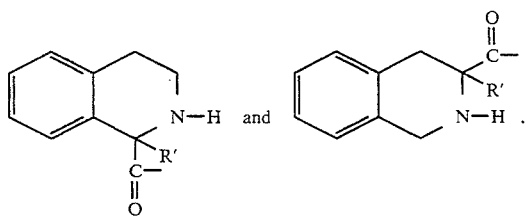

when R' is hydrogen, are referred to at times herein as 1- and 3-tetrahydro-isoquinolinecarboxylate, respectively, and are respectively abbreviated 1-Tiq and 3-Tiq.

The groups

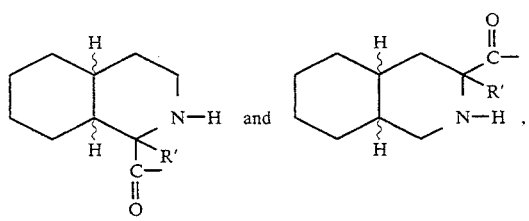

when R' is hydrogen, are referred to at times herein a 1- and 3-perhydro-isoquinolinecarboxylate, respectively, and are respectively abbreviated 1-Piq and 3-Piq. As indicated by the crooked lines, various ring fusion isomers of these substituents exist—this invention contemplates any individual isomer and combinations thereof.

The groups

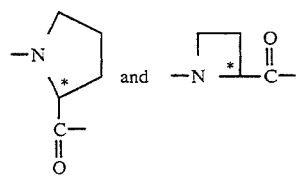

are referred to as prolinyl and azetidine-2-carboxyl, respectively, and are respectively abbreviated Pro and Azt.

The asterisks in Formula I and substituent Y denote a chiral center that is (L). The asterisk in substituent X denotes a chiral center that is (D) or (DL).

In addition, diastereomers may exist depending upon branching of alkyl substituents. The compounds of the present invention include mixtures of two or more diastereomers as well as each individual isomer.

The following compounds illustrate compounds contemplated within the scope of Formula I:

D-phenylalanyl-L-prolinyl-L-(α-methyl)arginine aldehyde;

D-phenylglycyl-L-azetidine-2-carbonyl-L-(α-methyl)arginine aldehyde;

D-1,2,3,4-tetrahydroisoquinolinyl-3-carbonyl-L-azetidine-2-carbonyl-L-(α-ethyl)arginine aldehyde;

D-2-naphthylalanine-L-azetidine-2-carbonyl-L-(α-methyl)arginine aldehyde; and

D-perhydroisoquinolinyl-1-carbonyl-L-prolinyl-L-(α-methyl)arginine aldehyde.

Preferred compounds of the present invention are those compounds of Formula I where A is hydrogen, X is MePhe, 1- or 3-Tiq, or 1- or 3-Piq, and Y is as defined above for Formula I, and pharmaceutically acceptable salts and solvates thereof.

As mentioned above, the invention includes pharmaceutically acceptable salts of the compounds defined by the above Formula I. A particular compound of this invention can possess one or more sufficiently basic functional groups, and accordingly react with any of a number of inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid, hydrobromic acid and sulfuric acid.

The compounds of the present invention are known to form hydrates and solvates with appropriate solvents. Preferred solvents for the preparation of solvate forms include water, alcohols, tetrahydrofuran, DMF, and DMSO. Preferred alcohols are methanol and ethanol. Other appropriate solvents may be selected based on the size of the solvent molecule. Small solvent molecules are preferred to facilitate the corresponding solvate formation. The solvate or hydrate is typically formed in the course of recrystallization or in the course of salt formation. One useful reference concerning solvates is Sykes, Peter, A Guidebook to Mechanism in Organic Chemistry, 6th Ed (1986, John Wiley & Sons, New York). As used herein, the term "solvate" includes hydrate forms, such as monohydrates and dihydrates.

The compounds of Formula I are prepared by known methods of peptide coupling. According to one such method the acid P-X'-COOH, where —X'-C(O)— has the same meaning as —X — defined for Formula I, and P is an amino protecting group, is coupled with a carboxy protected proline (or azetidine-2-carboxylic acid) to form the dipeptide (a). The carboxy protecting ester group of the proline or azetidine moiety is then removed (deblocked or de-esterified) and the free acid form of the dipeptide (b) is coupled with the lactam form of (αR)arginine (d). The above reaction sequence is illustrated by the following Scheme 1:

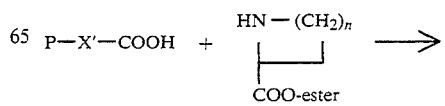

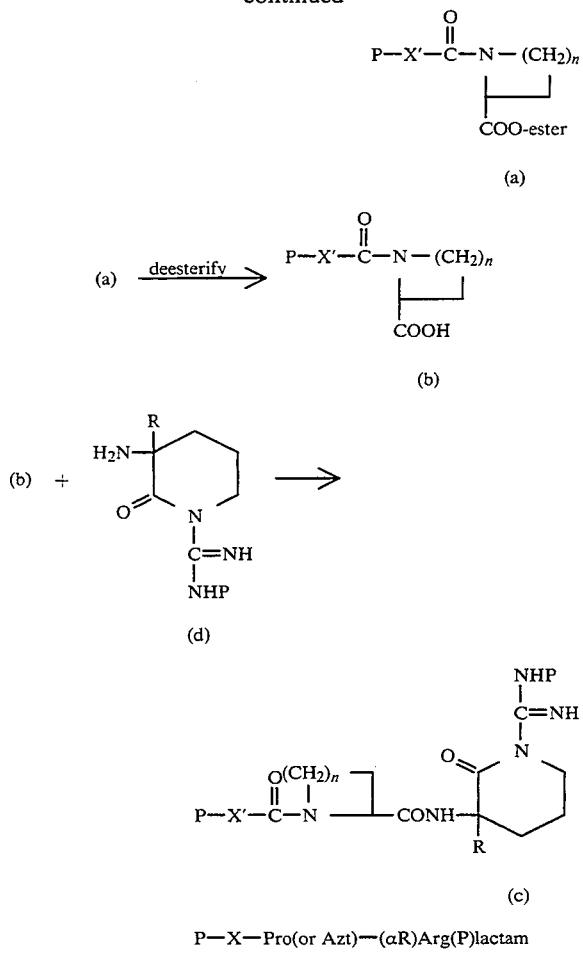

(a)

(b)

(d)

(c)

P—X—Pro(or Azt)—(αR)Arg(P)lactam wherein P represents an amino protecting group and n is 1 or 2.

The coupled (αR)Arg(P) lactam product (c) is reacted with a hydride reducing agent, preferably lithium aluminum hydride or lithium tri-tert-butoxyaluminohydride, in an inert solvent or mixture of solvents to reduce the lactam ring and provide the tripeptide in the arginine aldehyde form represented by the formula

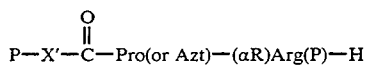

wherein (P) represents amino protecting groups.

The protecting groups are removed by procedures known to those skilled in the art such as hydrogenation over a metal catalyst.

The lactam form of (αR)arginine is obtained by intramolecular coupling of amino protected αR-substituted arginine [(αR)Arg-OH]. For example, Boc-(αR-)Arg(Cbz)OH represented by the formula

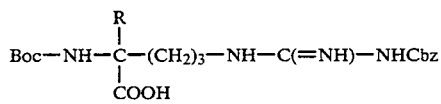

(e)

where Boc is t-butyloxycarbonyl and Cbz is benzyloxycarbonyl, is first converted to an active ester form, such as an active mixed anhydride, with a chloroformate ester, e.g. ethyl chloroformate to isobutyl chloroformate. The ester formation is carried out in the presence of a tertiary amine such as N-methylmorpholine. Addition of further or another tertiary amine base, such as triethylamine or diisopropylethylamine, effects the internal acylation to provide the lactam form of the diamino protected arginine as shown below

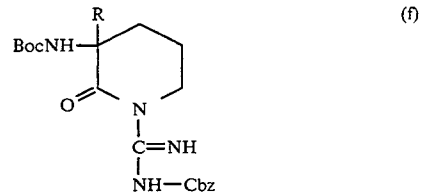

(f)

Prior to use in the coupling with the P-X'-(C=O)-Pro(or Azt)-OH as shown in the above scheme, the Boc or other amine protecting group is selectively removed with trifluoroacetic acid or HCl to provide the requisite free amino group.

The coupling of a P-X'-COOH compound with a proline or azetidine carboxylic ester is carried out by first protecting the amino group of the amino acid. Conventional amino protecting groups commonly used for temporary protection or blocking of the amino group are employed.

The amino-protecting group refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, t-butoxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4 -xenyl) isopropoxycarbonyl, 1,1-diphenyleth -1-yloxycarbonyl, 1,1-diphenylprop-1-yloxycarbonyl, 2-phenylprop- 2-yloxycarbonyl, 2-(p-toluyl) prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluoroenylmethoxycarbonyl ("FMOC"), 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)-phenylsulfenyl group, the diphenylphosphine oxide group, and the like amino-protecting groups. The species of amino-protecting group employed is not critical so long as the derivatized amino group is stable to the condition of subsequent reaction(s) on other positions of the molecule and can be removed at the appropriate point without disrupting the remainder of the molecule. Preferred amino-protecting groups are the benzyloxycarbonyl, allyloxycarbonyl, t-butoxycarbonyl, and trityl groups. Similar amino-protecting groups used in the cephalosporin, penicillin and peptide art are also embraced by the above terms. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

In carrying out the coupling reaction an ester protecting group for proline is employed which is removable by conditions under which the amino protecting group remains intact. The amino protecting group of the acylating acid P-X'-COOH thus remains in place for protection of the amino group during the subsequent coupling with the arginine lactam compound to form (c).

The carboxy protecting ester group as used in the specification refers to one of the ester derivatives of the carboxylic acid group commonly employed to block or protect the carboxylic acid group while reactions are carried out on other functional groups on the compound. Examples of such carboxylic acid protecting groups include $C_1$-$C_3$ alkyl, benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2', 4,4'-tetramethoxybenzhydryl, t-butyl, t-amyl, trityl, 4-methoxytrityl, 4,4'-dimethoxytrityt, 4,4', 4"-trimethoxytrityl, 2-phenylprop-2-yl, trimethylsilyl, t-butyldimethylsilyl, phenacyl, 2,2,2 -trichloroethyl, β-(trimethylsilyl)ethyl, β-(di(n-butyl)methylsilyl) ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) on other positions of the molecule and can be removed at the appropriate point without disrupting the remainder of the molecule. In particular, it is important not to subject the carboxy-protected molecule to strong nucleophilic bases or reductive conditions employing highly activated metal catalysts such as Raney nickel. (Such harsh removal conditions are also to be avoided when removing amino-protecting groups discussed below.) Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The compounds of Formula I can also be prepared by first synthesizing a Pro- (or Azt)-(αR)Arg dipeptide precursor and then reacting with a protected X-substituent. According to one such method, the cyclic lactam form of (αR)arginine (d) is prepared and coupled with an amino protected proline or azetidine-2-carboxylic acid (g) as shown below to afford the dipeptide (h)

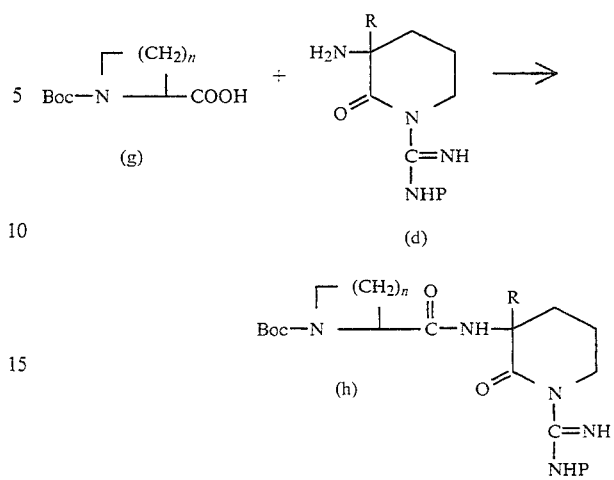

where P represents an amino protecting group such as the benzyloxycarbonyl (Cbz) group, t-butoxycarbonyl (Boc), p-toluenesulfonyl, and the like. Preferably the amino protecting group used is removable by hydrogenation or treatment with mild acid (e.g. trifluoroacetic acid) or a strong acid (e.g. HCl). Examples of other suitable amino protecting groups are provided in "Protective Groups in Organic Synthesis", Second Edition, by T. W. Greene and Peter G. M. Wuts, Chapter 7, page 309–405 (1991), John Wiley & Sons, Inc., publishers, incorporated herein by reference in its entirety. The Boc, or other suitable protecting group, is removed from the azetidine ring nitrogen which is then acylated with the desired amino acid acyl group to afford the tripeptide shown below.

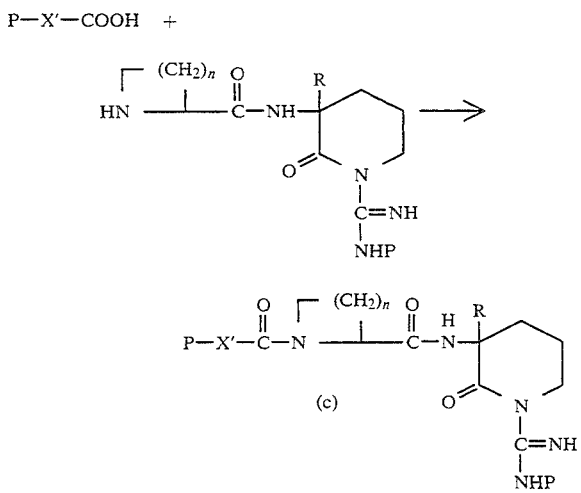

The coupled (αR)Arg(P) lactam product (c) is reduced and the protecting groups are removed as described earlier.

The coupling of an P-X'-COOH compound is carried out by first protecting the amino group of the amino acid. Conventional amino protecting groups commonly used for temporary protection or blocking of the amino group are employed. Examples of such protecting groups are described above.

The coupling reactions described above are carried out in the cold preferably at a temperature between about −20° C. and about 15° C. The coupling reactions are carried out in an inert organic solvent such as dimethylformamide, dimethylacetamide, tetrahydrofuran, methylene chloride, chloroform, and like common solvents or a mixture of such solvents. Generally anhydrous conditions are used when, in the coupling reaction, an active ester of the acylating acid is used.

The lactam intermediates (d) and (f) are prepared via standard techniques of organic chemistry as summarized in the following scheme:

priate conditions and in an appropriate order to allow for subsequent transformations.

The compounds of the invention are isolated best in the form of acid addition salts. Salts of the compounds of Formula I formed with acids such as those mentioned above are useful as pharmaceutically acceptable salts for administration of the antithrombotic agents and for preparation of formulations of these agents. Other acid addition salts may be prepared and used in the isolation

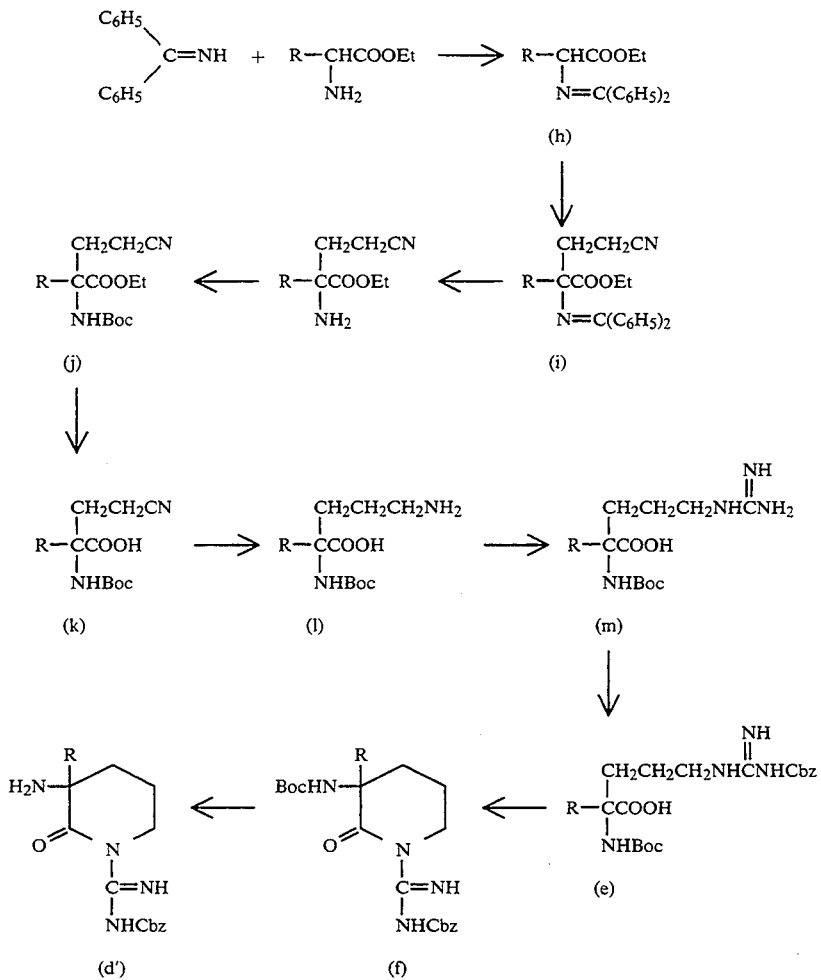

According to the above sequence, benzophenone imine can be used to protect alanine (R=methyl) or 2-aminobutyric acid (R=ethyl) to provide the protected amino acid (h). The precursor to the arginine group is introduced by alkylating (h) with an α-halopropionitrile to give (i). After deblocking the amine and reblocking with a protecting group more suitable for the subsequent reactions, such as a Boc group (e.g., intermediate (j)),the amino acid is first deesterified (k) and reduced to give the ornithine intermediate (l). Treatment with O-methylisourea in base provides the arginine derivative (m). The primary amine is blocked, e.g., with a Cbz functionality, to give (e) which is then cyclized as described above to give (f). Removing the Boc protecting group yields a primary amine (d') which is then used to couple to the mono- or di-peptide. As will be appreciated by skilled artisans, one may choose other protecting groups so long as they serve the purpose of protecting the functional group during subsequent chemistry but can also be removed under approand purification of the peptides. For example, the salts formed with the sulfonic acids such as methanesulfonic acid, n-butanesulfonic acid, p-toluenesulfonic acid and naphthalenesulfonic acid may be so used.

The preferred method for purifying the compounds of Formula I, while at the same time preparing a desired stable salt form, is that described in U.S. Pat. No. 5,250,660. According to the method, stable sulfates or hydrochlorides are provided by preparative purification over $C_{18}$ reversed-phase chromatography in which the aqueous component comprises sulfuric acid or hydrochloric acid at pH 2.5 and acetonitrile as the organic component. The pH of the acidic eluant is adjusted to between about pH 4 and about 6 with an anion exchange resin in the hydroxyl form e.g. Bio-Rad AG-1×8. After adjustment of the pH, the solution of tripeptide sulfate or hydrochloride salt is lyophilized to provide the pure salt in dry powder form. In an example of the process, crude D-MePhe-Pro-Arg(αMe)-H sulfate is dissolved in water and the solution is loaded on Vydac C₁₈ RP-HPLC 5 cm×50 cm column. A gradient of 2–10% B (A=0.01% $H_2SO_4$; B=acetonitrile) over 10 hours is used. Multiple fractions are collected and those containing product as determined by analytical RP-HPLC are pooled. The pH of the pooled fractions is adjusted to pH 4.0–4.5 with AG-1×8 resin in hydroxide form (Bio-Rad, 3300 Ragatta Blvd., Richmond, Calif. 94804). The solution is filtered and the filtrate is lyophilized to provide the pure D-,L-,L-, tripeptide in the form of the sulfate salt.

The optically active isomers of the diastereomers of the X substituent are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates and Resolutions,* John Wiley & Sons, 1981.

The compounds employed as initial starting materials in the synthesis of the compounds of this invention are well known and, to the extent not commercially available, are readily synthesized by standard procedures commonly employed by those of ordinary skill in the art.

The following Examples are provided to further describe the invention and are not to be construed as limitations thereof.

The R$_f$ values in the following examples unless otherwise stated, were determined by silica gel thin layer chromatography using Kieselgel 60F-254 (Merck, Darmstadt) in the following solvent systems:

(A) Chloroform-Methanol-Acetic Acid 135:15:1

(B) Ethyl acetate-Acetic Acid-Absolute Alcohol 90:10:10

(C) Chloroform-Methanol-Acetic Acid 90:30:5

The abbreviations used in the examples have the following meanings.

Amino acids: Arg=arginine, Pro=proline, Phe=phenylalanyl, 1-Tiq=1-tetrahydroisoquinolinecarboxylate Boc=t-butyloxycarbonyl
Cbz=benzyloxycarbonyl
DMF=dimethylformamide
EtOAc=ethyl acetate
Et₂O=diethyl ether
FAB-MS=fast atom bombardment mass spectrum
THF=tetrahydrofuran
TLC=thin layer chromatography Unless otherwise stated, pH adjustments and work up are with aqueous acid or base solutions.

EXAMPLE 1

D-N-methylphenylalanyl-L-prolinyl-L-α-methylarginine aldehyde (D-MePhe-Pro-Arg (αMe)-H)

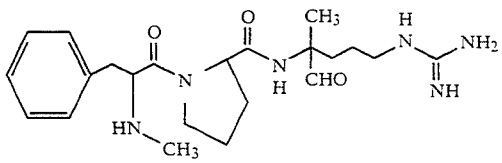

A) Preparation of ethyl Nᵅdiphenylmethylene-L-alaninate.

Benzophenone imine (53.4 g, 286 mmol) was dissolved in methylene chloride (400 mL) and stirred at room temperature. To the solution was added L-alanine ethyl ester (43.9 g, 286 mmol) and the reaction stirred at room temperature for 48 hours. The reaction was washed 3 times with water (200 mL). The organic layer was separated, dried (MgSO₄), and the filtrate was concentrated in vacuo to give a clear oil. The oil was crystallized from pentane to give the title compound (72.1 g, 90%), FAB-MS 282 (MH⁺).

Analysis for $C_{18}H_{19}NO_2$:
Calculated: C, 76.84; H, 6.81; N, 4.98.
Found: C, 76.73; H, 6.68; N, 5.22.

B) Preparation of ethyl Nᵅdiphenylmethylene-DL-(α-propionitrile)alaninate.

A solution of ethyl Nᵅdiphenylmethylene-L-alaninate (20 g, 71.2 mmol) in anhydrous THF (300 mL) was added to 18-crown-6 (18.8 g, 71.2 mmol), potassium hydride (17.8 g, 106.8 mmol), and THF (100 mL), and stirred under an inert atmosphere. The reaction was cooled to 0° C. and bromopropionitrile (8.9 mL, 106.8 mmol) dissolved in THF (20 mL) was added dropwise. The reaction was warmed to room temperature and stirred (2 hours). To the reaction was added a solution containing glacial acetic acid (6.5 mL), water (25 mL), and THF (20 mL) dropwise. The reaction was diluted with ethyl acetate and water. The organic layer was separated, washed 3 times with water, and dried (MgSO₄). The filtrate was concentrated in vacuo to give an oil. The crude oil was dissolved in methylene chloride/cyclohexane and chromatographed over silica gel. A step gradient system consisting of (A) hexane and (B) EtOAc was used to elute the pure compound. The gradient used was an increasing concentration of EtOAc from 0% to 25%. Fractions were collected and pooled on the basis of TLC profile. The combined fractions were concentrated in vacuo to give a clear oil of the title compound (15.5 g, 65%), FAB-MS 335 (MH⁺).

C) Preparation of ethyl DL-(α-propionitrile)alaninate.

A solution of ethyl Nᵅdiphenylmethylene-DL-(αpropionitrile)-alaninate (15.2 g, 45.4 mmol) in diethyl ether (90 mL) was cooled to 0° C. To the reaction was added 1 N HCl (54 mL) dropwise. The reaction was warmed to room temperature and stirred (24 hours). The aqueous layer was separated and extracted 3 times with diethyl ether. The aqueous layer separated and concentrated in vacuo to give a clear oil of the title compound (9.7 g, 100%), FAB-MS 171 (MH⁺).

D) Preparation of ethyl N$^\alpha$t-butyloxycarbonyl-DL-($\alpha$-propionitrile)alaninate.

A solution of ethyl DL-($\alpha$-propionitrile)alaninate (7.8 g, 37.8 mmol) in THF (50 mL) was charged with diisopropylethylamine (6.6 mL, 37.8 mmol) and stirred at room temperature. Di-tert-butyl dicarbonate (9.6 mL, 41.6 mmol) was added and the reaction stirred (24 hours). The reaction was diluted with EtOAc/water and the organic layer separated. The organic solution was washed 2 times with 0.1 N HCl, dried (MgSO$_4$), and the filtrate concentrated in vacuo to give an oil. The oil was crystallized from pentane to give the title compound (7.45 g, 73%), FAB-MS 271 (MH+).

Analysis for C$_{13}$H$_{22}$N$_2$O$_4$:
Calculated: C, 57.76; H, 8.00; N, 10.36;
Found: C, 57.76; H, 8.30; N, 10.45.

E) Preparation of N$^\alpha$t-butyloxycarbonyl-DL-($\alpha$-propionitrile)alanine.

A solution of ethyl N$^\alpha$t-butyloxycarbonyl-DL-($\alpha$-propionitrile)-alaninate (12.6 g, 46.4 mmol) in THF (100 mL) and water (58 mL) was stirred and cooled (0° C.). To the reaction was added 1 N NaOH (47 mL, 47 mmol) and the solution was stirred at 0° C. for 30 minutes and at room temperature (4 hours). The organic solvent was evaporated in vacuo, and EtOAc (100 mL) and water (100 mL) were added to the residue. The aqueous layer was separated, the pH of the solution was adjusted to 2.8 with 3 N HCl, and ethyl acetate (150 mL) was added. The organic layer was separated, dried (MgSO$_4$), and the filtrate was concentrated in vacuo to give a clear oil. The oil was crystallized from EtOAc/pentane to give the title compound (9.7 g, 86%), FAB-MS 243 (MH+).

F) Preparation of N$^\alpha$t-butyloxycarbonyl-DL-($\alpha$Me) ornithine.

A solution of N$^\alpha$t-butyloxycarbonyl-DL-($\alpha$-propionitrile)alanine (10.8 g, 44.4 mmol) in ethyl alcohol (135 mL) was reacted with hydrogen over platinum oxide (3 g) at 60 psi in a Parr shaker apparatus for 24 hours at 60° C. The reaction mixture was filtered through a Celite ® pad, and the filtrate was concentrated in vacuo. The solid was triturated with a mixture of THF, diethyl ether, and pentane. The solid was filtered and dried to give pure title compound (8.2 g, 75%).

G) Preparation of N$^\alpha$t-butyloxycarbonyl-DL-($\alpha$Me) arginine.

A solution of N$^\alpha$t-butyloxycarbonyl-DL-($\alpha$Me)ornithine (7.6 g, 30.9 mmol) in water (80 mL) was adjusted to pH 10.5 with 2 N NaOH and O-methylisourea hydrogen sulfate (10.6 g, 61.7 mmol) was added. The reaction was stirred at room temperature for 48 hours. The reaction was cooled to 0° C., and the solid was filtered and dried in vacuo to give pure title compound (5.8 g, 61%), FAB-MS 289 (MH+).

H) Preparation of Boc-DL-Arg($\alpha$Me) (Cbz)-OH.

A solution of N$^\alpha$t-butyloxycarbonyl-DL-($\alpha$Me)arginine (5.7 g, 18.4 mmol) in water (50 mL) was adjusted to pH 13.4 with 5 N NaOH. The reaction was chilled to −5° C. and the pH was maintained at 13.2–13.5 using 5 N NaOH while adding benzyl chloroformate (11 mL, 73.5 mmol) dropwise. The reaction stirred for an additional 1 hour at −5° C. and diluted with H20 (100 mL) and Et$_2$O (100 mL). The aqueous layer was separated and extracted with Et$_2$O (100 mL). The aqueous layer was acidified to pH 3.0 with 4 N HCl and extracted with EtOAc (200 mL). The aqueous layer was extracted twice with EtOAc. The combined EtOAc layers were washed with water and dried (MgSO$_4$). The organic solution was concentrated to dryness in vacuo to give the title compound (3.9 g, 50%), FAB-MS 423 (MH+).

Analysis for C$_{20}$H$_{30}$N$_4$O$_6$:
Calculated: C, 56.86; H, 7.16; N, 13.26;
Found: C, 56.79; H, 7.18; N, 13.13.

I) Preparation of Boc-DL-Arg($\alpha$Me)(Cbz)-lactam.

A solution of Boc-DL-Arg($\alpha$Me)(Cbz)-OH (3.76 g, 8.9 mmol) in THF (80 mL) was cooled to −10° C. To the reaction mixture was added triethylamine (1.3 mL, 9.3 mmol) followed by isobutyl chloroformate (1.22 mL, 9.3 mmol). The reaction was stirred 5 minutes at −10° C. and an additional amount of triethylamine (1.3 mL, 9.3 mmol) was added. The reaction stirred for 1 hour at −10° C. and 24 hours at room temperature. The reaction was poured into 200 mL of ice-water and the resulting precipitate was filtered, washed with cold water, and the solid dried in vacuo. The solid was crystallized from diethyl ether to give pure title compound (3.4 g, 95%), FAB-MS 405 (MH+).

Analysis for C$_{20}$H$_{28}$N$_4$O$_5$:
Calculated: C, 59.39; H, 6.98; N, 13.85;
Found: C, 59.65; H, 7.16; N, 13.16.

J) Preparation of DL-Arg($\alpha$Me) (Cbz) -Lactam.HCl.

A solution of EtOAc (20 mL) saturated with gaseous HCl was added to a solution of Boc-DL-Arg($\alpha$Me)(Cbz)-lactam (3.03 g, 7.5 mmol) dissolved in CH$_2$Cl$_2$ (10 mL) at room temperature. The reaction was allowed to stir 30 minutes at room temperature. The resulting precipitate was filtered washed with diethyl ether, and dried in vacuo to give the pure title compound (2.58 g, 100%), FAB-MS 305 (MH+).

K) Preparation of Cbz-D-MePhe-Pro-Arg($\alpha$Me)(Cbz)-Lactam.

A solution Cbz-D-MePhe-Pro-OH (1.64 g, 3.2 mmol) in DMF (40 mL) was cooled to 0° C. To the solution was added 1-hydroxybenzotriazole (0.44 g, 3.2 mmol), dicyclohexyl -carbodiimide (0.67 g, 3.2 mmol), DL-Arg($\alpha$Me)(Cbz)-Lactam.HCl (1.1 g, 3.2 mmol), and diisopropyl-ethylamine (0.84 mL, 4.8 mmol). The reaction was stirred for 1 hour at 0° C. and 48 hours at room temperature. The reaction precipitate was filtered and the filtrate concentrated in vacuo to an oil. The oil was dissolved in EtOAc (200 mL) and water (100 mL). The organic layer was separated, and washed sequentially with 1 N NaHCO$_3$, water, 1.5 N citric acid, and water. The organic layer was dried (MgSO$_4$), and the filtrate evaporated to an amorphous solid. The crude solid was dissolved in chloroform and chromatographed over silica gel. A step gradient system consisting of (A) chloroform and (B) acetonitrile was used to elute the correct diastereomeric peptide. The gradient used was an increasing concentration of CH$_3$CN from 0% to 50%. Fractions were collected and pooled on the basis of TLC profile. The combined fractions were concentrated in vacuo to give a clear oil of the title compound (0.71 g, 32%), FAB-MS 697 (MH+).

L) Preparation of Cbz-D-MePhe-Pro-Arg(αMe)(Cbz)-H.

Cbz-D-MePhe-Pro-Arg(αMe)(Cbz)-Lactam (0.67 g, 0.962 mmol) was dissolved in anhydrous THF (35 mL) and placed in a flask under an inert atmosphere. The reaction cooled to −65° C. and lithium aluminum hydride 1M in THF (1.0 mL, 1.0 mmol) was added dropwise. The reaction was stirred for 35 minutes at −65° C. A solution of 5 mL of THF and 0.8 mL of 0.5 N $H_2SO_4$ was added dropwise and the reaction was diluted with EtOAc (100 mL) and water (50 mL). The organic layer was separated, washed once with water, and dried ($MgSO_4$). The filtrate was concentrated to dryness in vacuo to an amorphous solid to give the title compound (0.74 g, 115%): TLC $R_f$(A) 0.45.

M) Preparation of D-MePhe-Pro-Arg((αMe)-H.

Cbz-D-MePhe-Pro-Arg(αMe)(Cbz)-H (0.74 g, 1.05 mmol) was dissolved in ethanol (75 mL), water (25 mL), and 1 N HCl (1.9 mL, 1.9 mmol), and hydrogenated in the presence of 5% Pd/C catalyst (0.45 g) at ambient temperature and pressure. After the reaction was completed, the catalyst was removed by filtration through a Hyflo ® pad. The filtrate was concentrated in vacuo down to 20 mL and water (50 mL) was added. The pH of solution adjusted to 4.0 with BioRad AG1-X8 resin ® (hydroxide form). The resin was removed by filtration and the solution lyophilized to give pure title compound as the dihydrochloride monohydrate (0.436 g, 90%), FAB-MS 431 (MH+); $[\alpha]_D = 102.9°$ (C=0.5/0.01 N HCl).

Analysis for $C_{22}H_{34}N_6O_3 \cdot 2HCl \cdot 1H_2O$:
Calculated: C, 50.67; H, 7.34; N, 16.12;
Found: C, 51.07; H, 6.90; N, 15.88.

EXAMPLE 2

D-1-(1,2,3,4-tetrahydroisoquinolinylcarboxyl)-L-prolinyl-L -α-methylarginine aldehyde (D-1-Tiq-Pro-Arg(αMe)-H)

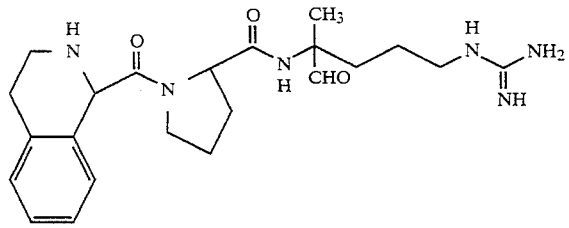

Following the procedure described above for Example 1, the title compound was prepared as the dihydrochloride salt. FAB-MS 429 (MH+); $[\alpha]_D = -36.1°$ (C=0.5/0.01 N HCl).

Analysis for $C_{22}H_{32}N_6O_3 \cdot 2HCl$:
Calculated: C, 52.69; H, 6.83; N, 16.76;
Found: C, 52.40; H, 6.61; N, 16.57.

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis. Further, the compounds of the present invention are believed to be orally active.

The invention in one of its aspects provides a method of inhibiting thrombin in mammals comprising administering to a mammal in need of treatment an effective (thrombin inhibiting) dose of a compound of formula I.

The thrombin inhibition contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disease states in which the compounds have a potential utility are in treatment or prophylaxis of thrombosis and hypercoagulability in blood and tissues. Disease states in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in prophylaxis of atherosclerotic diseases such as coronary arterial disease, cerebral arterial disease and peripheral arterial disease. Further, the compounds are expected to be useful together with thrombolytics in myocardial infarction. Further, the compounds have expected utility in the treatment or prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, and inflammatory diseases, including arthritis and diabetes. The anti-coagulant compound is administered orally, or parenterally, e.g., by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, and the condition being treated.

A typical daily dose for each of the above utilities is between about 0.01 mg/kg and about 1000 mg/kg. The dose regime may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent, e.g., tissue plasminogen activator (tPA), modified tPA, streptokinase or urokinase. In cases when clot formation has occurred and an artery or vein is blocked, either partially or totally, a clot lysing agent is usually employed. A compound of the invention can be administered prior to or along with the lysing agent or subsequent to its use alone and preferably further is administered along with aspirin to prevent the reoccurrence of clot formation.

The method of this invention is also practiced in conjunction with a platelet glycoprotein receptor (IIb-/IIIa) antagonist, that inhibits platelet aggregation. A compound of the invention can be administered prior to or along with the IIb/IIIa antagonist or subsequent to its use to prevent the reoccurrence of clot formation.

The method of this invention is also practiced in conjunction with aspirin. A compound of the invention can be administered prior to or along with aspirin or subsequent to its use to prevent the reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of Formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent, e.g., physiological saline (0.9%), 5% dextrose, Ringer's solution, and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Therefore, another embodiment of the present invention is a pharmaceutical formulation comprising an effective amount of a compound of Formula I or a pharmaceutically acceptable salt or solvate thereof in association with a pharmaceutically acceptable carrier, diluent or excipient therefor.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recipient thereof. The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like. The compositions of this invention may be formulated so as to provide quick, sustained, or delayed release of the active ingredient after administration to the patient by employing procedures well known in the art.

The following formulation examples are illustrative only and are not intended to limit the scope of the invention in any way. "Active ingredient," of course, means a compound according to Formula I or a pharmaceutically acceptable salt or solvate thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| | |
|---|---|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 mL dose, are made as follows:

| | |
|---|---|
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8.

An intravenous formulation may be prepared as follows:

| | |
|---|---|
| Active ingredient | 100 mg |
| Isotonic saline | 1,000 mL |

The solution of the above ingredients generally is administered intravenously to a subject at a rate of 1 mL per minute.

The compounds provided by the invention (Formula I) are orally active and selectively inhibit the action of thrombin in mammals.

The ability of the compounds of the present invention to be an effective and orally active thrombin inhibitor is evaluated in one or more of the following assays.

The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide.

The assay is carried out by mixing 50 μL buffer (0.03M Tris, 0.15M NaCl, pH 7.4) with 25 μL of bovine thrombin or human thrombin solution (0.21 mg/mL of thrombostat bovine thrombin, Parke-Davis, or purified human thrombin, Enzyme Research Laboratories, South Bend, Ind., at about 8 NIH units/mL, in the same buffer) and 25 μL of test compound in a solvent (in 50% aqueous methanol, v:v). The 150 μL of an aqueous solution of the chromogenic substrate (at 0.25 mg/mL) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

$$\text{Thrombin} + I \rightleftharpoons \text{Thrombin} - I$$

$$Kass = \frac{[\text{Thrombin} - I]}{[(\text{Thrombin}) \times (I)]}$$

Kass is calculated for a range of concentrations of test compounds and the mean value is reported in units of liter per mole.

By substantially following the procedures described above for human thrombin, and using other human blood coagulation system serine proteases and proteases of the fibrinolytic system with the appropriate chromogenic substrates, identified below, selectivity of the compounds of the present invention with respect to the coagulation factor serine proteases and with respect to the fibrinolytic system serine proteases are evaluated as well as their substantial lack of interference with serine proteases of the fibrinolytic system. Thrombin inhibitors preferably should spare fibrinolysis induced by urokinase, tissue plasminogen activator (t-PA) and streptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952 incorporated by reference herein in its entirety. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); pyroglutamyl-Pro-Arg-p-nitroanilide (for Factor XIa and for aPC); H-D-Pro-Phe-Arg-p-nitroanilide (for factor XIIa); and pyroglutamyl-Gly-Arg-p-nitroanilide (for urokinase); are purchased from KabiVitrum, Stockholm, Sweden, or from Midwest Biotech, Fishers, Ind.. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants or purchased from Midwest Biotech, Fishers, Ind..

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Table 1 which follows lists the Kass values obtained with the indicated compound represented by the Formula I.

TABLE 1

| | Inhibition Properties | | | | |
|---|---|---|---|---|---|
| | $K_{ass} \times 10^6$ (L/mole) | | | | |
| Example | Bovine Thrombin | Trypsin | Plasmin | Xa | t-PA |
| 1 | 1.1 | 0.004 | 0.0005 | 0.0003 | 0 |
| 2 | 0.22 | 0.014 | 0.0008 | 0.001 | 0 |

Materials

Dog plasma is obtained from conscious mixed-breed hounds (either sex Hazelton-LRE, Kalamazoo, Mich., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased form Leo Pharmaceuticals, Denmark, as 2200 Ploug units/vial. Streptokinase is purchased from Hoechst-Roussel Pharmaceuticals, Somerville, N.J.

Methods-Effects on Lysis of Human Plasma Clots by t-PA

Human plasma clots are formed in micro test tubes by adding 50 μL thrombin (73 NIH unit/mL) to 100 μL human plasma which contains 0.0229 μCi 125-iodine labeled fibrinogen. Clot lysis is studied by overlaying the clots with 50 μL of urokinase or streptokinase (50, 100, or 1000 unit/mL) and incubating for 20 hours at room temperature. After incubation the tubes are centrifuged in a Beckman Microfuge. 25 μL of supernate is added into 1.0 mL volume of 0.03M tris/0.15M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 ug/mL concentrations. Rough approximations of IC50 values are estimated by linear extrapolations from data points to a value which would represent 50 percent of lysis for that particular concentration of fibrinolytic agent.

Anticoagulant Activity

Materials

Dog plasma and rat plasma is obtained from conscious mixed-breed hounds (either sex, Hazelton-LRE, Kalamazoo, Mich., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents ACTIN, Thromboplastin, and Human plasma are from Baxter Healthcare Corp., Dade Division, Miami, Fla.

Bovine thrombin from Parke-Davis (Ann Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous shunt model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood circulated through the shunt for 15 minutes before the thread is carefully removed and weighed. The weight of a wet thread is subtracted from the total weight of the thread and thrombus (see J. R. Smith, *Br. J. Pharmacol.*, 77,29 (1982)).

$FeCl_3$ model of arterial injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20%) is expressed in terms of the actual weight of $FeCl_3$ only. To injure the artery and induce thrombosis, 2.85 µl is pipetted into the cuff to bathe the artery above the thermocouple probe. Arterial occlusion is indicated by a rapid drop in temperature. The time to occlusion is reported in minutes and represented the elapsed time between application of $FeCl_3$ and the rapid drop in vessel temperature (see K. D. Kurz, *Thromb. Res.*, 60, 269 (1990)).

Spontaneous thrombolysis model

In vitro data suggested that the peptide thrombin inhibitors inhibit thrombin and other serine proteases, such as plasmin and tissue plasminogen activator. To assess if the compounds inhibited fibrinolysis in vivo, the rate of spontaneous thrombolysis is determined by implanting a labeled whole blood clot into the pulmonary circulation. Rat blood (1 mL) is mixed rapidly with bovine thrombin (4 IU, Parke Davis) and $^{125}I$ human fibrogen (5 µCi, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected cpm} - \text{lung cpm})}{\text{injected cpm}} \times 100$$

The fibrinolytic dissolution of the implanted clot occurs time-dependently (see J. P. Clozel, *Cardiovas. Pharmacol.*, 12, 520 (1988)).

Coagulation parameters

Plasma thrombin time (TT) and activated partial thromboplastin time (APTT) are measured with a fibrometer. Blood is sampled from a jugular catheter and collected in syringe containing sodium citrate (3.8%, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and $CaCl_2$ (0.01 mL, 0.025 M) is added to start coagulation. Assays are done in duplicate and averaged.

Index of Bioavailability

A measure of bioactivity, plasma thrombin time (TT), served as a substitute for the assay of parent compound on the assumption that increments in TT resulted from thrombin inhibition by parent only. The time course of the effect of the thrombin inhibitor upon TT is determined after i.v. bolus administration to anesthetized rats and after oral treatment of fasted conscious rats. Due to limitations of blood volume and the number of points required to determine the time course from time of treatment to the time when the response returned to pretreatment values, two populations of rats are used. Each sample population represented alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{AUC \text{ po}}{AUC \text{ iv}} \times \frac{\text{Dose iv}}{\text{Dose po}} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the FeCl3 model of arterial injury and in the spontaneous thombosis model. Bolus injection volume is 1 mL/kg for i.v., and 5 mL/kg for p.o. and infusion volume is 3 mL/hr.

Statistics

Results are expressed as means +/− SEM. One-way analysis of variance is used to detect statistically significant differences and then Dunnett's test is applied to determine which means are different. Significance level for rejection of the null hypothesis of equal means is $P < 0.05$.

Animals

Male dogs (Beagles; 18 months-2 years; 12-13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66°-74° F.; 45-50% relative humidity; and lighted from 0600-1800 hours.

Pharmacokinetic model

Test compound is formulated immediately prior to dosing by dissolving in sterile 0.9% saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are derivatized with dinitrophenylhydrazine and analyzed by HPLC (Zorbax SB-C8 column) eluting with methanol/500 mM sodium acetate adjusted to pH 7 with phosphoric acid (60:40, v/v). Plasma concentration of test compound is recorded and used to calculate the pharmacokinetic parameters: elimination rate constant, $K_e$; total clearance, $C_{lt}$; volume of distribution, $V_D$; time of maximum plasma test compound concentration, $T_{max}$; maximum concentration of test compound at $T_{max}$, $C_{max}$; plasma half-life, to 0.5; area under the curve, A.U.C.; and fraction of test compound absorbed, F.

Canine Model of Coronary Artery Thrombosis

Surgical preparation and instrumentation of the dogs are as described in Jackson, et al., *Circulation*, 82, 930-940 (1990). Mixed-breed hounds (aged 6-7 months, either sex, Hazelton-LRE, Kalamazoo, Mich., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon ®-coated, 30-gauge silverplated copper wire) 3-4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40-50% inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formulation and Compound Administration Regimens

Electrolytic injury of the intima of the LCX is produced by applying 100-$\mu$A direct current (DC) to the anode. The current is maintained for 60 minutes and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/h is begun simultaneously with an infusion of thrombotic agent (e.g. tissue plasminogen activator, streptokinase, APSAC). Reperfusion is followed for 3 hours after administration of test compound. Reocclusion of coronary arteries after successful thrombolysis is defined as zero CBF which persisted for $\geq 30$ minutes.

Hematology and template bleeding time determinations

Whole blood cell counts, hemoglobin, and hematocrit values are determined on a 40-$\mu$l sample of citrated (3.8%) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide$\times 2$ mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 minutes), 60 minutes into infusion, at conclusion of administration of the test compound (120 minutes), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p < 0.05$. All values are mean$\pm$SEM. All studies are conducted in accordance with the guiding principles of the American Physiological Society.

Further details regarding the procedures are described in Jackson, et al., *J. Cardiovasc. Pharmacol.*, 21, 587–599 (1993).

We claim:

1. A compound having the formula

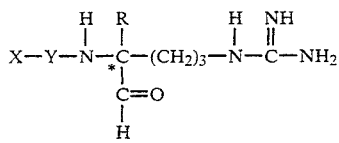

wherein
X is

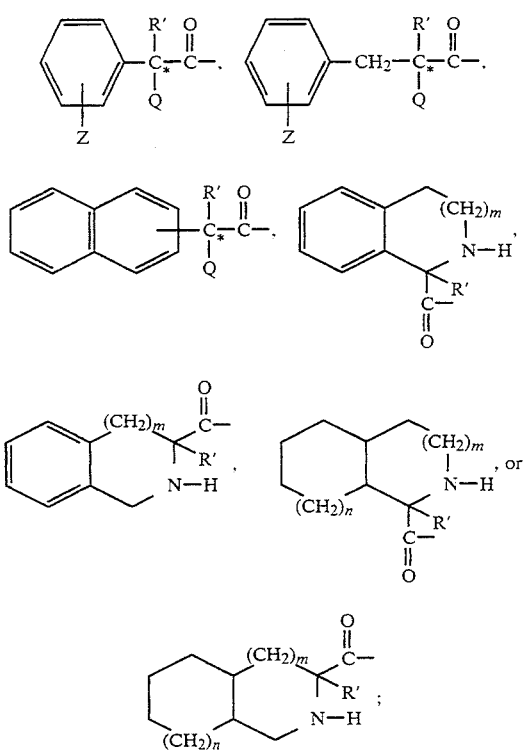

Q is —OH, $C_1$–$C_4$ alkoxy, or —NH—A;

A is hydrogen, $C_1$–$C_4$ alkyl, acetyl, $CF_3C(O)$—, $CF_3CF_2C(O)$—, R"$SO_2$—, benzyloxycarbonyl, or t-butyloxycarbonyl;

R' is hydrogen, $C_1$–$C_4$ alkyl, phenyl, or benzyl;

R" is $C_1$–$C_4$ alkyl, —$(CH_2)_d$—COOH, or unsubstituted or substituted aryl or heteroaryl, where aryl is phenyl or naphthyl, and heteroaryl is a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

d is 1, 2, or 3;
m is 0, 1, or 2;
n is 0, 1, or 2;
Y is

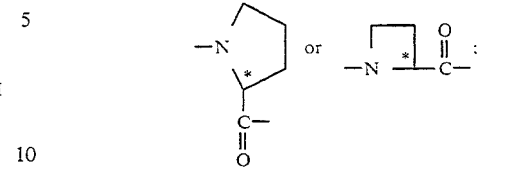

R is methyl or ethyl; and

Z is hydrogen, $C_1$–$C_4$ alkyl, $C_1$–$C_4$ alkoxy, hydroxy, halo, or $R_aSO_2NH$—, where $R_a$ is $C_1$–$C_4$ alkyl;

or a pharmaceutically acceptable salt thereof or a pharmaceutically acceptable solvate of said compound of formula I or salt thereof.

2. A compound of claim 1 where X is MePhe, 1- or 3-Tiq, or 1- or 3-Piq, or a pharmaceutically acceptable salt thereof or a pharmaceutically acceptable solvate of said compound or salt thereof.

3. A compound of claim 2 where R is methyl, or a pharmaceutically acceptable salt thereof or a pharmaceutically acceptable solvate of said compound or salt thereof.

4. A compound of claim 3 which is D-1-(1,2,3,4-tetrahydroisoquinolinylcarboxyl)-L-prolinyl-L-α-methylarginine aldehyde or a pharmaceutically acceptable salt thereof or a solvate of said compound or salt thereof.

5. A compound of claim 3 which is D-N-methylphenylalanyl-L-prolinyl-L-α-methylarginine aldehyde or a pharmaceutically acceptable salt thereof or a solvate thereof.

6. A pharmaceutical formulation comprising a compound of claim 1 or a pharmaceutically acceptable salt thereof or a pharmaceutically acceptable solvate of said compound or salt thereof, in association with a pharmaceutically acceptable carrier, diluent, or excipient therefore.

7. A formulation of claim 6 where X is MePhe, 1- or 3-Tiq, or 1- or 3-Piq.

8. A formulation of claim 7 where R is methyl.

9. A formulation of claim 8 where said compound is D-N-methylphenylalanyl-L-prolinyl-L-α-methylarginine aldehyde.

10. A formulation of claim 8 where said compound is (1,2,3,4-tetrahydroisoquinolinylcarboxyl)-L-prolinyl-L-α-methylarginine aldehyde.

11. A method of inhibiting thrombin in mammals, comprising administering to a mammal requiring thrombin inhibition, an effective dose of a compound of claim 1 or a pharmaceutically acceptable salt thereof or a pharmaceutically acceptable solvate of said compound or salt thereof.

12. The method of claim 11 where X is MePhe, 1- or 3-Tiq, or 1- or 3-Piq.

13. The method of claim 12 where R is methyl.

14. The method of claim 13 where said compound is D-N-methylphenylalanyl-L-prolinyl-L-α-methylarginine aldehyde.

15. The method of claim 13 where said compound is (1,2,3,4-tetrahydroisoquinolinylcarboxyl)-L-prolinyl-L-α-methylarginine aldehyde.

* * * * *